US006753305B2

(12) United States Patent
Raso et al.

(10) Patent No.: US 6,753,305 B2
(45) Date of Patent: Jun. 22, 2004

(54) PROCESS FOR DISINFECTING A HARD-SURFACE WITH A COMPOSITION COMPRISING CINNAMON OIL AND/OR AN ACTIVE THEREOF

(75) Inventors: Floriana Raso, Rome (IT); Alberto Caselli, Terni (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/256,810

(22) Filed: Sep. 27, 2002

(65) Prior Publication Data

US 2003/0083222 A1 May 1, 2003

Related U.S. Application Data

(63) Continuation of application No. PCT/US01/11928, filed on Apr. 12, 2001.

(51) Int. Cl.$^7$ .............................................. C11D 17/00
(52) U.S. Cl. ..................... 510/438; 510/180; 510/182; 510/238; 510/218; 510/463; 512/1; 512/3; 424/65
(58) Field of Search ................................ 510/438, 180, 510/182, 238, 218, 463, 101, 102, 105, 106, 107; 512/1, 3; 424/65

(56) References Cited

U.S. PATENT DOCUMENTS

| | | | | |
|---|---|---|---|---|
| 5,554,588 A | * | 9/1996 | Behan et al. | 512/1 |
| 6,001,789 A | * | 12/1999 | Trinh et al. | 510/191 |
| 6,194,362 B1 | * | 2/2001 | Trinh et al. | 510/101 |
| 6,537,955 B1 | * | 3/2003 | Raso et al. | 510/218 |

\* cited by examiner

*Primary Examiner*—Necholus Ogden
(74) *Attorney, Agent, or Firm*—Thibault Fayette; Kim William Zerby; Steven W. Miller

(57) ABSTRACT

The present invention relates to a process of disinfecting a hard-surface with a composition comprising cinnamon oil and/or an active thereof whereby disinfecting benefits are provided.

10 Claims, No Drawings

PROCESS FOR DISINFECTING A HARD-SURFACE WITH A COMPOSITION COMPRISING CINNAMON OIL AND/OR AN ACTIVE THEREOF

CROSS REFERENCE TO RELATED APPLICATIONS

This is a continuation of International Application PCT/US01/11928 with an international filing date of Apr. 12, 2001, published in English under PCT Article 21(2) which claims benefit of European Application No. 00870072.6, filed Apr. 14, 2000.

TECHNICAL FIELD

The present invention relates to a process for disinfecting various hard-surfaces like walls, tiles, table tops, glass, bathroom surfaces, kitchen surfaces as well as dishes.

BACKGROUND

Hard-surfaces, like walls, tiles, table tops, glass as well as dishes, are prone to contamination with micro-organisms like bacteria, including Gram positive bacterial strains and Gram negative bacterial strains, viruses, and other more resistant micro-organisms like fungi. Hard-surfaces prone to contamination with micro-organisms can be found in various locations like: private households, for example, in kitchens and bathrooms; hospitals; restaurants; hotels; means of public transport; public bathes and pools; commercial and public laundries and the like.

Compositions for disinfecting hard-surfaces are well known in the art. Indeed, disinfecting compositions based on known disinfecting materials like bleach, quaternary ammonium compounds, essential oils or the like, provide acceptable disinfecting properties. For example, WO 97/25404 and WO 97/25106 describe disinfecting compositions based on essential oils and/or actives thereof in combination with hydrogen peroxide bleach.

Indeed, essential oils and/or actives thereof are known antimicrobial agents. Moreover, essential oils and/or actives thereof are, due to their availability from natural sources, preferable ingredients in hard-surface disinfectants. Indeed, it is well known from consumer research that consumers are looking for products comprising natural ingredients. However, it is well known that the overall disinfecting performance of the disinfecting compositions comprising essential oils and/or actives thereof used to disinfect hard-surfaces may still be further improved.

It is therefore an objective of the present invention to provide a process of disinfecting a hard-surface with a composition that delivers good overall disinfecting performance. In particular, it is an objective of the present invention to provide a process of disinfecting a hard-surface with a composition that delivers good disinfecting performance on Gram positive bacterial strains, like *Staphylococcus aureus* and Gram negative bacterial strains, like *Pseudomonas aeruginosa*, as well as on viruses and more resistant micro-organisms like fungi, under acidic, neutral and alkaline pH conditions.

It has now been found that the above objectives can be met by a process of disinfecting a hard-surface with a composition comprising cinnamon oil and/or an active thereof.

An advantage of the process as described herein is that said process provides an easy and fast way of disinfecting a hard-surface.

Another advantage of the present invention is that disinfection is provided on a broad range of bacterial strains including Gram positive bacterial strains, like *Staphylococcus aureus*, Gram negative bacterial strains, like *Pseudomonas aeruginosa*, viruses and more resistant micro-organisms like fungi, under acidic, neutral and alkaline pH conditions.

It is yet another advantage of the invention to provide a process of disinfecting a hard-surface with a composition that is mild to the skin as well as safe to the hard-surfaces treated therewith.

Another advantage of the present invention is that cinnamon oil and actives thereof are ingredients coming from natural sources and/or are present in nature.

BACKGROUND ART

The following documents are representative of the prior art available in the field of disinfecting compositions used on various surfaces.

EP 0 252 278 describes liquid mucous membrane disinfectants based on alcohol and hydrogen peroxide containing one or more carboxylic acids, nitrogen-containing organic compounds from the group of specific oligohexamethyl biguanides, and optionally microbiocidically active phenolic compounds as well as water.

WO 97/25404 and WO 97/25106 describe liquid disinfectant preparations for use on hard-surfaces comprising an essential oil or an active thereof.

SUMMARY OF THE INVENTION

The present invention encompasses a process of disinfecting hard-surfaces with a composition comprising cinnamon oil and/or an active thereof.

In a preferred embodiment, said composition comprises cinnamon acid, cinnamyl alcohol and/or cinnamyl aldehyde as an active of cinnamon oil.

In another preferred embodiment said composition is a liquid, preferably liquid aqueous, composition.

In another preferred embodiment said composition further comprises another essential oil and/or active thereof on top of the cinnamon oil and/or an active thereof, preferably an essential oil and/or active thereof selected from the group consisting of thymol and geraniol and mixtures thereof.

DETAILED DESCRIPTION OF THE INVENTION

Process of Disinfecting a Hard-surface

The present invention encompasses a process of disinfecting a hard-surface with a composition, as defined herein, said process preferably comprising the step of applying said composition onto said surface.

The hard-surfaces to treat with the compositions herein are those typically found in houses like kitchens, bathrooms, e.g., tiles, walls, floors, chrome, glass, smooth vinyl, any plastic, plastified wood, table top, sinks, cooker tops, dishes, sanitary fittings such as sinks, showers, shower curtains, wash basins, WCs and the like. Hard-surfaces also include household appliances including, but not limited to, refrigerators, freezers, washing machines, automatic dryers, ovens, microwave ovens, dishwashers and so on. Furthermore, hard-surfaces found in hospitals, restaurants, hotels, means of public transport, public bathes and pools, commercial and public laundries and the like are included herein.

In such a process a composition, as described herein, needs to be contacted with the hard-surfaces to be disinfected. Thus, the present invention also encompasses a process of disinfecting a hard-surface with a composition as described herein, wherein said process comprises the step of applying said composition to said hard-surface, preferably only infected portions thereof and optionally rinsing said hard-surface.

In the process of disinfecting hard-surfaces according to the present invention the compositions as described herein may be in liquid form and may be applied to the surface to be disinfected in their neat form or in their diluted form typically at a dilution level up to 100 times their weight of a suitable solvent, preferably water, preferably into 80 to 2 times their weight of a suitable solvent, preferably water, and more preferably 60 to 10 times their weight of a suitable solvent, preferably water.

In a preferred embodiment wherein the composition herein is incorporated onto a wipe, the process of disinfecting a hard-surface comprises the steps of contacting said wipe incorporation a composition as described herein with said hard-surface and preferably wiping said hard-surface with said wipe.

The Composition

The compositions of the present invention are preferably formulated as liquid compositions. Preferred compositions herein are aqueous compositions and therefore, preferably comprise water, more preferably in an amount of from 60% to 98%, even more preferably of from 80% to 97% and most preferably 85% to 97% by weight of the total composition.

The pH of the liquid compositions according to the present invention may typically be from 1 to 14.

In a preferred embodiment according to the present invention, the liquid compositions according to the present invention have an alkaline pH. More preferably, the pH of the liquid compositions herein, as is measured at 25° C., is at least, with increasing preference in the order given, 7.1, 7.5, 8.0, 8.5, 9.0, 9.25, 9.5 or 9.75. Independently, the pH of the liquid compositions herein, as is measured at 25° C., preferably is no more than, with increasing preference in the order given, 14.0, 13.5, 13.0, 12.5, 12.0, 11.5, 11.0, 10.75, 10.5, 10.25 or 10. Accordingly, the compositions herein may further comprise an acid, alkaline material and/or a buffering system to adjust and maintain pH as appropriate.

In another preferred embodiment, the liquid compositions according to the present invention have an acidic pH. More preferably, the pH of the liquid compositions herein, as is measured at 25° C., is at least, with increasing preference in the order given, 0.1, 0.5, 1.0, 1.5, 2, 2.5 or 3.0. Independently, the pH of the liquid compositions herein, as is measured at 25° C., preferably is no more than, with increasing preference in the order given, 6.9, 6.5, 6.0, 5.5, 5.0, 4.5, 4.0, 3.5 or 3.25. Accordingly, the compositions herein may further comprise an acid, alkaline material and/or a buffering system to adjust and maintain pH as appropriate. These preferred pH ranges also contribute to the stability of hydrogen peroxide, when present.

In still another preferred embodiment, the liquid compositions according to the present invention have a neutral pH.

Preferred acids herein to adjust the pH are organic or inorganic acids or mixtures thereof, these acids may be added on top of the organic acids and slats thereof as described herein below. Preferred organic acids are acetic acid, lactic acid or citric acid or a mixture thereof. Preferred inorganic acids are sulfuric acid or phosphoric acid or a mixture thereof. A particularly preferred acid to be used herein is an inorganic acid and most preferred is sulfuric acid.

Typical levels of such acids, when present, are of from 0.01% to 5.0%, preferably from 0.05% to 3.0%, and more preferably from 0.05% to 2.5% by weight of the total composition.

The alkaline material to be used herein to adjust the pH can be organic or inorganic bases. Suitable bases for use herein are the caustic alkalis, such as sodium hydroxide, potassium hydroxide and/or lithium hydroxide, and/or the alkali metal oxides such, as sodium and/or potassium oxide or mixtures thereof. A preferred base is a caustic alkali, more preferably sodium hydroxide and/or potassium hydroxide.

Other suitable bases include ammonia, ammonium carbonate and hydrogen carbonate.

Typical levels of such bases, are of from 0.01% to 5.0%, preferably from 0.05% to 3.0%, and more preferably from 0.05% to 2.5% by weight of the total composition.

Cinnamon Oil and/or an Active Thereof

As an essential ingredient the compositions according to the present invention comprise cinnamon oil and/or an active thereof.

By "active of cinnamon oil", it is meant herein any ingredient of cinnamon oil that exhibits antimicrobial activity.

Preferred actives of cinnamon oil are selected from the group consisting of cinnamic acid ($C_6H_5CH=CHCOOH$; 3-phenyl-2-propenoic acid); cinnamyl aldehyde ($C_6H_5CH=CHCHO$; 3-phenyl-2-propenal); cinnamyl alcohol ($C_6H_5CH=CHCH_2OH$; 3-phenyl-2-propen-1-ol); dehydro-cinnamyl aldehyde; amyl cinnamyl aldehyde; hexyl cinnamyl aldehyde; hexyl cinnamyl aldehyde; and α-n-butyl cinnamyl aldehyde; and mixtures thereof. More preferred actives of cinnamon oil are selected from the group consisting of: cinnamic acid ($C_6H_5CH=CHCOOH$; 3-phenyl-2-propenoic acid) and cinnamyl aldehyde ($C_6H_5CH=CHCHO$; 3-phenyl-2-propenal); and mixtures thereof. An even more preferred active of cinnamon oil is cinnamyl aldehyde ($C_6H_5CH=CHCHO$; 3-phenyl-2-propenal).

Cinnamon oil is commercially available from Sigma. Cinnamic acid is commercially available from Sigma. Cinnamyl alcohol is commercially available from Aldrich. Cinnamyl aldehyde is commercially available from Aldrich under the tradename trans-cinnamyl aldehyde. Dehydro-cinnamyl aldehyde is commercially available from Aldrich under the tradename Hydrocinnamyl aldehyde. Amyl cinnamyl aldehyde is commercially available from Aldrich under the tradename (α-Amyl cinnamyl. Hexyl cinnamyl aldehyde is commercially available from Aldrich under the tradename (α-Hexyl cinnamyl aldehyde. (α-n-butyl cinnamyl aldehyde is commercially available from Aldrich under the tradename α-butyl cinnamyl aldehyde.

Typically, the cinnamon oil or active thereof or mixture thereof is present in the composition at a level up to 20%, preferably at a level of at least 0.003% to 10%, more preferably from 0.006% to 10%, even more preferably from 0.006% to 8% and most preferably from 0.006% to 3%, by weight of the total composition.

The present invention is based on the surprising finding that the use of cinnamon oil and/or an active thereof in a composition used to disinfect a hard-surface, provides disinfecting benefits. Indeed, it has been observed that the use of cinnamon oil and/or an active thereof in a composition used to disinfect a hard-surface provides a significant improvement in disinfecting performance compared to other compositions used to disinfect a hard-surface comprising another essential oil or an active thereof, as for example thymol, geraniol or eugenol.

Furthermore, it has been found that compositions used to disinfect hard-surfaces comprising cinnamon oil and/or an active thereof provide disinfecting benefits on a broad range of bacterial strains including Gram positive bacterial strains, like *Enterococcus hirae* and *Staphylococcus aureus*, Gram negative bacterial strains, like *Pseudomonas aeruginosa, Escherichia coli* and Salmonella, viruses and more resistant micro-organisms like fungi, present on infected surfaces. In particular, it has been found that such disinfecting compositions comprising cinnamon oil and/or an active thereof provide an excellent disinfecting performance ("disinfecting benefits") on both Gram positive bacterial strains and Gram negative bacterial strains, whereas other essential oils or actives thereof only provide disinfecting performance on either Gram positive bacterial strains or Gram negative bacterial strains.

Advantageously, the disinfection benefits are obtained with the compositions of the present invention even when used under highly diluted conditions, i.e., up to dilution levels of from 1:100 (composition:water).

Furthermore, the disinfection benefits are obtained under acidic, neutral and alkaline pH conditions.

Disinfecting Test Method

The disinfecting properties of a composition according to the present invention may be measured by the bactericidal activity of said composition. Test methods suitable to evaluate the bactericidal activity of a composition on infected surfaces are described in European Standard, EN 1040, EN 1276, dated September 1997 issued by the European committee for standardization, Brussels. European Standards EN 1040 and EN 1276 specify test methods and requirements for the minimum bactericidal activity of a disinfecting composition. The tests are passed if the bacterial colonies forming units (cfu) are reduced from a $10^7$ cfu (initial level) to a $10^2$ cfu (final level after contact with the disinfecting product), i.e., a $10^5$ reduction of the viability is necessary. Other suitable methods are the AOAC Use-dilution method, AOAC Germicidal Spray method, AOAC Wipes method (US) and AFNOR T72-190 (Europe). The AFNOR method NF T72-190 (France, Europe) is described in the French Standard and was issued in August 1988.

Optional Ingredients

Essential Oil or Active Thereof

As an optional but highly preferred ingredient the compositions according to the present invention may comprise an essential oil or an active thereof or a mixture thereof in addition to the cinnamon oil or active thereof. Any essential oil or active thereof agent known to those skilled in the art to exhibit an antimicrobial activity may be used herein.

By "actives of essential oils", it is meant herein any ingredient of essential oils that exhibit antimicrobial activity.

It is speculated that said antimicrobial essential oils and actives thereof act as proteins denaturing agents. Also said antimicrobial-active essential oils and actives thereof are compounds which contribute to the safety profile of the compositions according to the present invention when used to disinfect any surface. A further advantage of said antimicrobial oils and actives thereof is that they impart pleasant odor to a composition comprising them without the need of adding a perfume.

Such essential oils include, but are not limited to, those obtained from thyme, lemongrass, citrus, lemons, oranges, anise, clove, aniseed, geranium, roses, mint, lavender, citronella, eucalyptus, peppermint, camphor, sandalwood, pine, vervain, rosmarin, fleagrass, ratanhiae and cedar and mixtures thereof.

Actives of essential oils for use herein include, but are not limited to, thymol (present for example in thyme), eugenol (present for example in clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, ferulic acid, methyl salicylic acid, methyl salicylate, terpineol and mixtures thereof.

Preferred actives of essential oils to be used herein are thymol, eugenol, verbenone, eucalyptol, terpineol, methyl salicylic acid and/or geraniol. More preferred actives of essential oils to be used herein are selected from the group consisting of thymol, eugenol, geraniol and mixtures thereof. Even more actives of essential oils to be used herein are selected from the group consisting of thymol and geraniol and mixtures thereof.

Thymol is commercially available for example from Aldrich, eugenol is commercially available for example from Sigma, Systems—Bioindustries (SBI)—Manheimer Inc., cinnamic acid is commercially available for example from Aldrich and cinnamyl aldehyde is commercially available for example from Aldrich.

Typically, the antimicrobial essential oil or active thereof or mixture thereof is present in the composition at a level up to 20%, preferably from 0.003% to 10%, more preferably from 0.006% to 10%, even more preferably from 0.006% to 8% and most preferably from 0.006% to 3%, by weight of the total composition.

In a preferred embodiment of the present invention, the compositions herein comprise a binary essential oil and/or active thereof system. By "binary essential oil and/or active thereof system" it is meant herein that in addition to the cinnamon oil and/or active thereof, the composition comprises one additional essential oil and/or active thereof (first additional essential oil and/or active). Preferably, said additional essential oil and/or active thereof is selected from the group consisting of eugenol, thymol and geraniol, more preferably selected from the group consisting of thymol and geraniol. Preferably, said binary essential oil and/or active thereof system comprises from 0.001% to 20%, preferably from 0.001% to 10%, by weight of the total composition of cinnamon oil and/or an active thereof; and from 0.001% to 10%, preferably from 0.001% to 5%, by weight of the total composition of the first additional essential oil and/or active thereof, preferably thymol or geraniol or eugenol, more preferably thymol or geraniol.

In another highly preferred embodiment of the present invention, the compositions herein comprise a ternary essential oil and/or active thereof system. By "ternary essential oil and/or active thereof system" it is meant herein that in addition to the cinnamon oil and/or active thereof, the composition comprises two additional essential oils and/or actives thereof (first and second additional essential oil and/or active). Preferably, said two additional essential oils and/or actives thereof are thymol and geraniol. Preferably, said ternary essential oil and/or active thereof system comprises from 0.001% to 20%, preferably from 0.001% to 10%, by weight of the total composition of cinnamon oil and/or an active thereof; from 0.001% to 10%, preferably from 0.001% to 5%, by weight of the total composition of the first additional essential oil and/or active thereof, preferably thymol; and from 0.001% to 10%, preferably from 0.001% to 5%, by weight of the total composition of the second additional essential oil and/or active thereof, preferably geraniol.

Indeed, it has been found that in the preferred embodiments herein, wherein the cinnamon oil and/or active thereof as described above, is combined with one or two other essential oils in a binary or a ternary essential oil system, the disinfecting properties of the compositions herein are even further increased compared to the compositions comprising cinnamon oil and/or an active thereof alone.

Organic Acid or a Salt Thereof

As an optional but highly preferred ingredient the compositions according to the present invention may comprise an organic acid or a salt thereof or a mixture thereof. Any organic acid or salt thereof known to those skilled in the art may be used herein. Organic acids and salts thereof, when present, contribute to the disinfection properties of the compositions described herein.

Suitable organic acids or salts thereof are selected from the group consisting of mono- and poly-carboxylic acids, percarboxylic acids and substituted carboxylic acids, and salts thereof, and mixtures thereof.

Suitable mono- and poly-carboxylic acids or salts thereof are selected from the group consisting of citric acid, lactic acid, ascorbic acid, isoascorbic acid, tartaric acid, formic acid, maleic acid, malic acid, malonic acid, propionic acid, acetic acid, dehydroacetic acid, benzoic acid, hydroxy benzoic acid, and salts thereof, and mixtures thereof.

Suitable percarboxylic acids or salts thereof are selected from the group consisting of peracetic acid, percarbonic acid, perboric acid, and salts thereof, and mixtures thereof.

Suitable substituted carboxylic acids or salts thereof are selected from the group consisting of aminoacids, halogenated carboxylic acids, and salts thereof, and mixtures thereof.

Preferred organic acids or salts thereof for use herein are selected from the group consisting of lactic acid, citric acid, and ascorbic acid and salts thereof and mixtures thereof. More preferred organic acids for use herein are selected from the group consisting of lactic acid and citric acid and salts thereof and mixtures thereof. An even more preferred organic acids for use herein is lactic acid or a salt thereof.

Suitable organic acids or salts thereof are commercially available from JBL, T&L, or Sigma. Lactic acid is commercially available from Sigma and Purac.

Typically the composition herein may comprise up to 20%, preferably from 0.1% to 10%, more preferably from 0.1% to 5%, even more preferably from 0.1% to 3%, by weight of the total composition of an organic acid or a salt thereof.

The Disinfecting Material

As an optional ingredient the compositions according to the present invention may comprise a disinfecting material or a mixture thereof, preferably an effective amount of a disinfecting material or a mixture thereof, in addition to the cinnamon oil and/or active thereof and the other essential oil and/or active thereof, when present.

By "disinfecting material", it is meant herein any known ingredient having the ability of reducing or even eliminating by killing the micro-organisms existing on a surface, not already listed herein above.

By "an effective amount of a disinfecting material", it is meant herein an amount sufficient to allow the disinfecting material to perform its action, i.e., to reduce the number of micro-organisms existing on a given surface. Depending on the disinfecting material used the amount used may be different. Typically, the compositions of the present invention comprise from 0.001% to 40%, preferably from 0.05% to 10% and more preferably from 0.1% to 5% by weight of the total composition of a disinfecting material.

Suitable disinfecting materials herein are all those known by those skilled in the art for the purpose of disinfecting and may include : bleaches like peroxygen bleaches and/or chlorine-type bleaches; quaternary ammonium compounds; phenolic compounds; aldehydes like glutaraldehyde and formaldehyde; glyoxal; parabens like ethyl paraben, propyl paraben, methyl paraben; biguanide antimicrobial agents; peroxy acids; and mixtures thereof.

Preferred disinfecting materials for use herein include a peroxygen bleach, or a biguanide antimicrobial agent or a mixture thereof.

A preferred disinfecting material for use herein is a peroxygen bleach or a mixture thereof. Preferred peroxygen bleach is hydrogen peroxide, or a water soluble source thereof, or mixtures thereof. Hydrogen peroxide is most preferred to be used herein.

The presence of the peroxygen bleach, especially hydrogen peroxide, in the compositions according to the present invention contribute to the disinfection properties of said compositions. Indeed, said peroxygen bleach may attack the vital function of the micro-organism cells, for example, it may inhibit the assembling of ribosomal units within the cytoplasm of the micro-organisms cells. Also the peroxygen bleach, like hydrogen peroxide, is an oxidizer that generates hydroxyl free radicals which attack proteins and nucleic acids. Furthermore, the presence of the peroxygen bleach, especially hydrogen peroxide, provides good stain removal benefits when used in any hard surface application.

As used herein a hydrogen peroxide source refers to any compound which produces hydrogen peroxide when said compound is in contact with water. Suitable water-soluble sources of hydrogen peroxide for use herein include percarbonates, persilicates, persulphates such as monopersulfate, perborates and peroxyacids such as diperoxydodecandioic acid (DPDA), magnesium perphthalic acid and mixtures thereof.

In addition, other classes of peroxides can be used as an alternative to hydrogen peroxide and sources thereof or in combination with hydrogen peroxide and sources thereof. Suitable classes include dialkylperoxides, diacylperoxides, preformed percarboxylic acids, organic and inorganic peroxides and/or hydroperoxides.

Typically, peroxygen bleach or a mixture thereof is present in the compositions according to the present invention at a level up to 20%, preferably from 0.1% to 15%, and more preferably from 0.5% to 10% by weight of the total composition.

Other suitable disinfecting materials for use herein include chlorine-type bleaches like hypochlorite.

Suitable quaternary ammonium compounds for use herein are quaternary ammonium compounds containing alkyl or substituted alkyl groups, alkyl amide and carboxylic acid groups, ether groups, unsaturated alkyl groups, and cyclic quaternary ammonium compounds, which can be chlorides, dichlorides, bromides, methylsulphates, chlorophenates, cylcohexylsulphamates or salts of the other acids. Among the possible cyclic quaternary ammonium compounds are the following:

alkylpyridinium chlorides and/or sulphates, the alkyl group being preferably cetyl, dodecyl or hexadecyl group;

alkylisoquinolyl chlorides and/or bromides, the alkyl group being preferably dodecyl group. Particularly suitable quaternary ammonium compounds for use herein include alkyl dimethyl benzyl ammonium chloride, octyl decyl dimethyl ammonium chloride, dioctyl dimethyl ammonium chloride, dodecyl dimethyl ammonium chloride, alkyl dimethyl ammonium saccharinate, cetylpyridinium and mixtures thereof.

Suitable phenolic compounds for use herein include o-phenyl-phenol, o-benzyl (p-chlorophenol), 4-tertamylphenol and mixtures thereof.

Suitable biguanide antimicrobial agents are characterised in comprising at least one, preferably 2 or more, biguanide moieties according to the following formula:

Suitable and preferred biguanide antimicrobial agents are oligo- or poly alkylene biguanides or salts thereof or mixtures thereof. More preferred biguanide antimicrobial agents are oligo- or poly hexamethylene biguanides or salts thereof or mixtures thereof.

Examples of suitable biguanide antimicrobial agent are describe in EP 0 024 031, U.S. Pat. Nos. 2,684,924, 2,990, 425, 3,468,898, 4,022,834, DE-OS-22 12 259 and DE-OS-26 27 548. Particularly suitable biguanide antimicrobial agents are select from the group consisting of poly (hexamethylene biguanide) hydrochloride, 1,2-Bis-($N^5$-p-chlorphenyl-$N^1$-biguanide)-ethane, 1,2-Bis-($N^5$-p-nitrophenyl-$N^1$-biguanide)-ethane, 1,2-Bis-($N^5$-p-hydroxyphenyl-$N^1$-biguanide)-ethane, 1,2-Bis-($N^5$-p-chlorbenzyl-$N^1$-biguanide)-ethane, 1,2-Bis-($N^5$-p-bromphenyl-$N^5$-hexyl-$N^1$-biguanide)-ethane, 1,2-Bis-($N^5$-p-chlorphenyl-$N^5$-2-ethylphenyl-$N^1$-biguanide)-ethane, 1,2-Bis-($N^5$-p-chlorphenyl-$N^1$-ethyl-$N^1$-biguanide)-ethane, 1,2-Bis-($N^5$-p-methoxyphenyl-$N^1$-biguanide)-ethane, 1,2-Bis-($N^5$-p-methylphenyl-$N^1$-biguanide)-ethane, 1,2-Bis-($N^5$-3, 5-dimethylphenyl-$N^1$-biguanide)-ethane, 1,2-Bis-($N^5$-2,6-dichlorphenyl-$N^1$-biguanide)-ethane, 1,2-Bis-($N^5$-2,6-dimethylphenyl-$N^1$-biguanide)-ethane, 1,4-Bis-($N^5$-p-chlorphenyl-$N^1$-biguanide)-butane, Bis-($N^5$-p-chlorphenyl-$N^1$-biguanide)-methane, 1,3-Bis-($N^5$-p-chlorphenyl-$N^1$-biguanide)-propane and 1,1'-hexamethylene-bis-[5-(4-chlorphenyl)-biguanide] and salts thereof, and mixtures thereof.

In a preferred embodiment according to the present invention said biguanide antimicrobial agents is a poly hexamethylene biguanide or salt thereof according to the following formula:

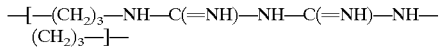

wherein n is an integer selected from 1 to 50, preferably 1 to 20, more preferably 12. More preferably said biguanide antimicrobial agents is a salt of a poly hexamethylene biguanide according to the following formula:

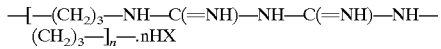

wherein n is an integer selected from 1 to 50, preferably 1 to 20, more preferably 12, and HX is salt component, preferably HCl.

A suitable poly hexamethylene biguanide or salt thereof is poly (hexamethylene biguanide) hydrochloride (PBG) wherein in the above formula n=12, commercially available under the trade name Vantocil IB® or Cosmocil CQ® from Avecia.

In another preferred embodiment according to the present invention said biguanide antimicrobial agents is 1,1'-hexamethylene-bis-[5-(p-chlorphenyl)-biguanide], commercially available under the trade name Chlrohexidine®.

Preferred biguanide antimicrobial agents according to the present invention are poly (hexamethylene biguanide) hydrochloride, preferably having a polymerization degree of 12, 1,1'-hexamethylene-bis-[5-(p-chlorphenyl)-biguanide] and mixtures thereof. A more preferred biguanide antimicrobial agents according to the present invention is poly (hexamethylene biguanide) hydrochloride, preferably having a polymerization degree of 12.

Typically the composition herein may comprise up to 20%, preferably from 0.01% to 20%, more preferably from 0.01% to 10%, even more preferably from 0.01% to 5%, by weight of the total composition of a biguanide antimicrobial agent.

Optional Ingredients
Surfactants

The compositions according to the present invention may further comprise a surfactant or mixtures thereof. Suitable surfactants to be used herein may be any surfactant known to those skilled in the art including anionic, nonionic, cationic, amphoteric and/or zwitterionic surfactants. Surfactants contribute to the cleaning performance of the disinfecting compositions of the present invention.

Particularly suitable anionic surfactants to be used herein include water soluble salts or acids of the formula $ROSO_3M$ wherein R is preferably a $C_6$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyl-diphenyl-ether-sulphonates and alkyl-carboxylates. Other anionic surfactants can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14}$–$C_{16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides, such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO$—$M^+$ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred anionic surfactants for use in the compositions herein are the alkyl benzene sulfonates, alkyl sulfates, alkyl alkoxylated sulfates, paraffin sulfonates and mixtures thereof.

Suitable amphoteric surfactants to be used herein include amine oxides having the following formula $R_1R_2R_3NO$ wherein each of $R_1$, $R_2$ and $R_3$ is independently a saturated substituted or unsubstituted, linear or branched hydrocarbon chains of from 1 to 30 carbon atoms. Preferred amine oxide surfactants to be used according to the present invention are amine oxides having the following formula $R_1R_2R_3NO$ wherein $R_1$ is an hydrocarbon chain comprising from 1 to 30 carbon atoms, preferably from 6 to 20, more preferably from 8 to 16, most preferably from 8 to 12, and wherein $R_2$ and $R_3$ are independently substituted or unsubstituted, linear or branched hydrocarbon chains comprising from 1 to 4 carbon atoms, preferably from 1 to 3 carbon atoms, and more preferably are methyl groups. $R_1$ may be a saturated substituted or unsubstituted, linear or branched hydrocarbon chain.

Suitable amine oxides for use herein are for instance natural blend $C_8$–$C_{10}$ amine oxides as well as $C_{12}$–$C_{16}$ amine oxides commercially available from Hoechst.

Suitable zwitterionic surfactants to be used herein contain both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylates and sulfonates, although other groups like sulfates, phosphonates, and the like can be used. A generic formula for some zwitterionic surfactants to be used herein is

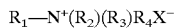

wherein $R_1$ is a hydrophobic group; $R_2$ and $R_3$ are each $C_1$–$C_4$ alkyl, hydroxy alkyl or other substituted alkyl group which can also be joined to form ring structures with the N; $R_4$ is a moiety joining the cationic nitrogen atom to the hydrophilic group and is typically an alkylene, hydroxy alkylene, or polyalkoxy group containing from 1 to 10 carbon atoms; and X is the hydrophilic group which is preferably a carboxylate or sulfonate group. Preferred hydrophobic groups $R_1$ are alkyl groups containing from 1 to 24, preferably less than 18, more preferably less than 16 carbon atoms. The hydrophobic group can be unsaturated and/or contain substituents and/or linking groups such as aryl groups, amido groups, ester groups and the like. In general, the simple alkyl groups are preferred for cost and stability reasons.

Highly preferred zwitterionic surfactants include betaine and sulphobetaine surfactants, derivatives thereof or mixtures thereof. Said betaine or sulphobetaine surfactants are preferred herein as, they help disinfection by increasing the permeability of the bacterial cell wall, thus allowing other active ingredients to enter the cell.

Furthermore, due to the mild action profile of said betaine or sulphobetaine surfactants, they are particularly suitable for the cleaning of delicate surfaces, e.g., surfaces in contact with food and/or babies. Betaine and sulphobetaine surfactants are also extremely mild to the skin and/or surfaces to be treated.

Suitable betaine and sulphobetaine surfactants to be used herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference. Preferred betaine and sulphobetaine surfactants herein are according to the formula:

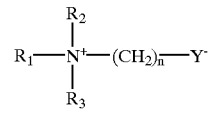

wherein $R_1$ is a hydrocarbon chain containing from 1 to 24 carbon atoms, preferably from 8 to 18, more preferably from 12 to 14, wherein $R_2$ and $R_3$ are hydrocarbon chains containing from 1 to 3 carbon atoms, preferably 1 carbon atom, wherein n is an integer from 1 to 10, preferably from 1 to 6, more preferably is 1, Y is selected from the group consisting of carboxyl and sulfonyl radicals and wherein the sum of $R_1$, $R_2$ and $R_3$ hydrocarbon chains is from 14 to 24 carbon atoms, or mixtures thereof.

Examples of particularly suitable betaine surfactants include $C_{12}$–$C_{18}$ alkyl dimethyl betaine such as coconut-betaine and $C_{14}$–$C_{16}$ alkyl dimethyl betaine such as lauryl-betaine. Coconut-betaine is commercially available from Seppic under the trade name of Amonyl 265®. Lauryl-betaine is commercially available from Albright & Wilson under the trade name Empigen BB/L®.

Other specific zwitterionic surfactants have the generic formulas:

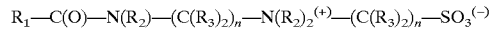

or

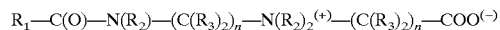

wherein each $R_1$ is a hydrocarbon, e.g. an alkyl group containing from 8 up to 20, preferably up to 18, more preferably up to 16 carbon atoms, each $R_2$ is either a hydrogen (when attached to the amido nitrogen), short chain alkyl or substituted alkyl containing from one to 4 carbon atoms, preferably groups selected from the group consisting of methyl, ethyl, propyl, hydroxy substituted ethyl or propyl and mixtures thereof, preferably methyl, each $R_3$ is selected from the group consisting of hydrogen and hydroxy groups and each n is a number from 1 to 4, preferably from 2 to 3, more preferably 3, with no more than one hydroxy group in any $(C(R_3)_2)$ moiety. The $R_1$ groups can be branched and/or unsaturated. The $R_2$ groups can also be connected to form ring structures. A surfactant of this type is a $C_{10}$–$C_{14}$ fatty acylamidopropylene(hydroxypropylene)sulfobetaine that is available from the Sherex Company under the trade name "Varion CAS sulfobetaine"®.

Suitable nonionic surfactants to be used herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Particularly suitable for use herein as nonionic surfactants are hydrophobic nonionic surfactants having an HLB (hydrophilic-lipophilic balance) below 16, preferably below 15, more preferably below 12, and most preferably below 10. Those hydrophobic nonionic surfactants have been found to provide good grease cutting properties.

Preferred hydrophobic nonionic surfactants to be used in the compositions according to the present invention are surfactants having an HLB below 16 and being according to the formula $RO$—$(C_2H_4O)_n(C_3H_6O)_mH$, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and, n and m are from 0.5 to 15, more preferably n+m is from 1 to 10 and, n and m are from 0 to 10. The preferred R chains for use herein are the $C_8$ to $C_{22}$ alkyl chains. Accordingly, suitable hydrophobic nonionic surfactants for use herein are Dobanol$^R$ 91-2.5 (HLB=8.1; R is a mixture of C9 and $C_{11}$ alkyl chains, n is 2.5 and m is 0), or Lutensol$^R$ TO3 (HLB=8; R is a $C_{13}$ alkyl chains, n is 3 and m is 0), or Lutensol$^R$ AO3 (HLB=8; R is a mixture of $C_{13}$ and $C_{15}$ alkyl chains, n is 3 and m is 0), or Tergitol$^R$ 25L3 (HLB=7.7; R is in the range of $C_{12}$ to $C_{15}$ alkyl chain length, n is 3 and m is 0), or Dobanol$^R$ 23-3 (HLB=8.1; R is a mixture of $C_{12}$ and $C_{13}$ alkyl chains, n is 3 and m is 0), or Dobanol$^R$ 23-2 (HLB=6.2; R is a mixture of $C_{12}$ and $C_{13}$ alkyl chains, n is 2 and m is 0), or Dobanol$^R$ 45-7 (HLB=11.6; R is a mixture of $C_{14}$ and $C_{15}$ alkyl chains, n is 7 and m is 0) Dobanol$^R$ 23-6.5 (HLB=11.9; R is a mixture of $C_{12}$ and $C_{13}$ alkyl chains, n is 6.5 and m is 0), or Dobanol$^R$ 25-7 (HLB=12; R is a mixture of $C_{12}$ and $C_{15}$ alkyl chains, n is 7 and m is 0), or Dobanol$^R$ 91-5 (HLB=11.6; R is a mixture of $C_9$ and $C_{11}$ alkyl chains, n is 5 and m is 0), or Dobanol$^R$ 91-6 (HLB=12.5; R is a mixture of $C_9$ and $C_{11}$ alkyl chains, n is 6 and m is 0), or Dobanol$^R$ 91-8 (HLB=13.7; R is a mixture of $C_9$ and $C_{11}$ alkyl chains, n is 8 and m is 0), Dobanol$^R$ 91-10 (HLB=14.2; R is a mixture of $C_9$ to $C_{11}$ alkyl chains, n is 10 and m is 0), or mixtures thereof. Preferred herein are Dobanol$^R$ 91-2.5, or Lutensol$^R$ TO3, or Lutensol$^R$ AO3, or Tergitol$^R$ 25L3, or Dobanol$^R$ 23-3, or Dobanol $^R$ 23-2, or mixtures thereof. These Dobanol$^R$ surfactants are commercially available from SHELL. These Lutensol$^R$ surfactants are commercially available from BASF and these Tergitol$^R$ surfactants are commercially available from UNION CARBIDE.

Typically, the surfactant or mixtures thereof may be present in the composition of the present invention at a level of from 0.01% to 50% by weight of the total composition, preferably from 0.01% to 30% and more preferably from 0.05% to 20%.

Cleaning Test Method

Standard enamel plates are soiled by applying on them a grease/particulate matter and then baking them. The tested compositions are applied on a sponge that is placed onto a Gardner Machine. The Gardner machine measures the number of strokes needed to reach 95–99% clean plates. The performance is measured as such (i.e., undiluted) and upon dilution at 1.5% in water.

Chelating Agents

The compositions herein may further comprise a chelating agent as a preferred optional ingredient. Suitable chelating agents may be any of those known to those skilled in the art such as the ones selected from the group comprising phosphonate chelating agents, amino carboxylate chelating agents or other carboxylate chelating agents, or polyfunctionally-substituted aromatic chelating agents or mixtures thereof.

Such phosphonate chelating agents may include etidronic acid (1-hydroxyethylidene-bisphosphonic acid or HEDP) as well as amino phosphonate compounds, including amino alkylene poly (alkylene phosphonate), alkali metal ethane 1-hydroxy diphosphonates, nitrilo trimethylene phosphonates, ethylene diamine tetra methylene phosphonates, and diethylene triamine penta methylene phosphonates. The phosphonate compounds may be present either in their acid form or as salts of different cations on some or all of their acid functionalities. Preferred phosphonate chelating agents to be used herein are diethylene triamine penta methylene phosphonates. Such phosphonate chelants are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987 to Hartman and Perkins. Ethylenediamine N,N'-disuccinic acid is, for instance, commercially available under the tradename ssEDDS® from Palmer Research Laboratories.

Suitable amino carboxylate chelating agents useful herein include ethylene diamine tetra acetates, diethylene triamine pentaacetates, diethylene triamine pentaacetate (DTPA), N-hydroxyethylethylenediamine triacetates, nitrilotriacetates, ethylenediamine tetrapropionates, triethylenetetraaminehexa-acetates, ethanoldiglycines, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein include malonic acid, salicylic acid, glycine, aspartic acid, glutamic acid, or mixtures thereof.

Said chelating agents, especially phosphonate chelating agents like diethylene triamine penta methylene phosphonates, are particularly preferred in the compositions according to the present invention as they have been found to further contribute to the disinfecting properties of the compositions herein.

Further chelating agents to be used herein include polymeric chelating agents, such as vinylpyrrolidone methacrylate copolymers, which are, for instance, commercially available from BASF under the trade name Luvitec VPMA 91W®.

Typically, the compositions according to the present invention comprise up to 5% by weight of the total composition of a chelating agent, or mixtures thereof, preferably from 0.002% to 3% by weight and more preferably from 0.002% to 1.5%.

Radical Scavengers

The compositions herein may further comprise a radical scavenger as a preferred optional ingredient. Suitable radical scavengers for use herein include the well-known substituted mono and di hydroxy benzenes and derivatives thereof, alkyl- and aryl carboxylates and mixtures thereof. Preferred radical scavengers for use herein include di-tert-butyl hydroxy toluene, hydroquinone, di-tert-butyl hydroqouine, mono-tert buytl hydroquinone, tert-butyl-hydroxy anysole, benzoic acid, toluic acid, catechol, t-butyl catechol, 2-methoxy-phenol, 2-ethoxy-phenol, 4-allyl-catechol, 2-methoxy-4-(2-propenyl)phenol, benzylamine, 1,1,3-tris(2-methyl-4-hydroxy-5-t-butylphenyl) butane, as well as n-propyl-gallate. Highly preferred for use herein is di-tert-butyl hydroxy toluene, which is for example commercially available from SHELL under the trade name IONOL CP®.

Typically, the compositions according to the present invention comprise up to 5% by weight of the total composition of a radical scavenger, or mixtures thereof, preferably from 0.01% to 1.5% by weight and more preferably from 0.01% to 1%.

Solvents

When used, solvents will, advantageously, give an enhanced cleaning and disinfecting performance to the composition. Suitable solvents for incorporation in the compositions according to the present invention include all those known to those skilled in the art of hard-surfaces cleaner compositions. For example, suitable solvents for use herein include ethers and diethers having from 4 to 14 carbon atoms, preferably from 6 to 12 carbon atoms, and more preferably from 8 to 10 carbon atoms, glycols or alkoxylated glycols, glycol ethers and/or derivatives, polyols, alkoxylated aromatic alcohols, aromatic alcohols, aliphatic branched or linear alcohols, alkoxylated aliphatic branched or linear alcohols, terpenes, and mixtures thereof.

Suitable glycols for use herein are according to the formula HO—$CR_1R_2$—OH wherein $R_1$ and $R_2$ are independently H or a $C_2$–$C_{12}$ saturated or unsaturated aliphatic hydrocarbon chain and/or cyclic. Suitable glycols to be used herein are dodecaneglycol, 1,2-hexanediol and/or propanediol.

Suitable alkoxylated glycols for use herein are according to the formula R—$(A)_n$—$R_1$—OH wherein R is H, OH, a linear saturated or unsaturated alkyl of from 1 to 20 carbon atoms, preferably from 2 to 15 and more preferably from 2 to 10, wherein $R_1$ is H or a linear saturated or unsaturated alkyl of from 1 to 20 carbon atoms, preferably from 2 to 15 and more preferably from 2 to 10, and A is an alkoxy group preferably ethoxy, methoxy, and/or propoxy and n is from 1 to 5, preferably 1 to 2. Suitable alkoxylated glycols to be used herein are methoxy octadecanol and/or ethoxyethoxyethanol.

Suitable glycol ethers and/or derivatives thereof for use herein include monoglycol ethers and/or derivatives thereof, di-, tri- and poly-glycol ethers and/or derivatives thereof and mixtures thereof.

Suitable monoglycol ethers and derivatives thereof for use herein include propylene glycol butyl ether, and water-soluble CELLOSOLVE® solvents or mixtures thereof. Preferred Cellosolve® solvents include 2-(Hexyloxy)ethanol (i.e., 2-hexyl Cellosolve®), ethylene glycol ethyl ether (i.e., 2-ethyl Cellosolve(®), ethylene glycol butyl ether (i.e., 2-butyl Cellosolve®) or mixtures thereof.

Suitable polyglycol ethers and derivatives thereof for use herein include n-butoxypropoxypropanol (n-BPP), butyl triglycol ether (BTGE), butyl diglycol ether (BDGE), diethylene glycol butyl ether, water-soluble CARBITOL® solvents or mixtures thereof.

Preferred water-soluble CARBITOL® solvents are compounds of the 2-(2-alkoxyethoxy)ethanol class, 2-(2-alkoxyethoxy)propanol class and/or 2-(2-alkoxyethoxy)butanol class wherein the alkoxy group is derived from ethyl, propyl, butyl and tert-butyl. A preferred water-soluble carbitol is 2-(2-butoxyethoxy)ethanol also known as butyl carbitol®.

Suitable polyols for use herein are aliphatic linear or branched saturated or unsaturated hydrocarbons having from 2 to 12 carbon atoms, preferably 4 to 10, and comprising at least 2 hydroxyl groups, preferably from 2 to 4. Suitable polyols herein are diols such as 2-ethyl-1,3-hexanediol, 2,2,4-trimethyl-1,3-pentanediol, methyl-2,4 pentanediol, 1,6-hexanediol or mixture thereof.

Suitable alkoxylated aromatic alcohols for use herein are according to the formula $R(A)_n$—OH wherein R is an alkyl substituted or non-alkyl substituted aryl group of from 1 to 20 carbon atoms, preferably from 2 to 15 and more preferably from 2 to 10, wherein A is an alkoxy group preferably butoxy, propoxy and/or ethoxy, and n is an integer of from 1 to 5, preferably 1 to 2. Suitable alkoxylated aromatic alcohols are benzoxyethanol and/or benzoxypropanol.

Suitable aromatic alcohols for use herein are according to the formula R—OH wherein R is an alkyl substituted or non-alkyl substituted aryl group of from 1 to 20 carbon atoms, preferably from 1 to 15 and more preferably from 1 to 10. For example a suitable aromatic alcohol to be used herein is benzyl alcohol.

Suitable aliphatic linear or branched alcohols for use herein are according to the formula R—OH wherein R is a branched or linear saturated or unsaturated alkyl group of from 1 to 20 carbon atoms, preferably from 2 to 15 and more preferably from 2 to 12. Particularly suitable aliphatic branched alcohols to be used herein include 2-ethylbutanol and/or 2-methylbutanol. Particularly suitable aliphatic linear alcohols to be used herein include decanol, ethanol and/or 1- or 2-propanol.

Suitable alkoxylated aliphatic linear or branched alcohols for use herein are according to the formula R—$(A)_n$—OH wherein R is a branched or linear saturated or unsaturated alkyl group of from 1 to 20 carbon atoms, preferably from 2 to 15 and more preferably from 5 to 12, wherein A is an alkoxy group preferably butoxy, propoxy and/or ethoxy, and n is an integer of from 1 to 5, preferably 1 to 2. Suitable alkoxylated aliphatic branched alcohols include 1-methylpropoxyethanol and/or 2-methylbutoxyethanol. Suitable alkoxylated aliphatic linear alcohols include ethoxy propanol and/or propoxy propanol.

Other suitable solvents include ter amilic alcohol, terpene solvents and the like.

Suitable terpenes for use herein are mono-and bicyclic terpenes, especially those of the hydrocarbon class, which include the terpinenes, terpinolenes and pinenes and mixtures thereof. Highly preferred materials of this type are dipentene, alpha-pinene and/or beta-pinene. For example, pinene is commercially available from SCM Glidco (Jacksonville) under the name Alpha Pinene P&F®.

Particularly preferred solvents for use herein are ethylene glycol butyl ether, propylene glycol butyl ether, diethylene glycol butyl ether, butoxy propoxy propanol, butyl diglycol ether, benzyl alcohol, butoxypropanol, 2-(2-butoxyethoxy) ethanol, ethanol, methanol, benzyl alcohol, isopropanol, 1-propanol and mixtures thereof.

Highly preferred solvent mixtures for use herein include:
2-(2-butoxyethoxy) (preferably at level of 0.1% to 5% by weight), butoxy propanol (preferably at level of 0.1% to 10% by weight), and benzyl alcohol (preferably at level of 0.1% to 2% by weight); or ethanol (preferably at level of 0.1% to 10% by weight), butoxy propanol (preferably at level of 0.1% to 10% by weight) and benzyl alcohol (preferably at level of 0.1% to 2% by weight); or ethanol (preferably at level of 0.1% to 10% by weight) and butoxy propanol (preferably at level of 0.1% to 10% by weight); or ethanol (preferably at level of 0.1% to 10% by weight) and 1-propanol (preferably at level of 0.1% to 10% by weight); or ethanol alone; or 1-propanol alone.

These solvent mixtures provide additional cleaning benefits in neat conditions and accelerate the evaporation time of the compositions comprising them, resulting in shorter cleaning time for the housewife.

Typically, the compositions of the present invention comprise up to 20% by weight of the total composition of a solvent or mixtures thereof, preferably from 0.5% to 10% by weight, more preferably from 1% to 8% and most preferably from 2% to 7% by weight of the composition.

Peroxygen Bleach

Another suitable additional component for use herein is a peroxygen bleach. Peroxygen bleach, especially hydrogen peroxide, persulfate and the like, in the compositions of the present invention advantageously contribute to the disinfection properties of said compositions. Hence, not to be bound by theory, it is believed that said peroxygen bleach may attack the vital function of the micro-organism cells, for example, it may inhibit the assembling of ribosomal units within the cytoplasm of the micro-organism cells. Also, said peroxygen bleach like hydrogen peroxide, is a strong oxidizer that generates hydroxyl free radicals which attack proteins and nucleic acids. Furthermore, the presence of said peroxygen bleach, especially hydrogen peroxide, provides strong stain removal benefits which are particularly noticeable for example in laundry and hard surfaces applications.

As used herein, a hydrogen peroxide source refers to any compound which produces hydrogen peroxide when said compound is in contact with water. Suitable water-soluble sources of hydrogen peroxide for use herein include percarbonates, persilicate, persulphate such as monopersulfate, perborates and peroxyacids such as diperoxydodecandioic acid (DPDA), magnesium perphthalic acid and mixtures thereof.

A preferred peroxygen bleach is hydrogen peroxide, or a water soluble source thereof, or mixtures thereof. A most preferred peroxygen bleach is hydrogen peroxide.

In addition to the peroxygen bleach, other classes of peroxides can be used as an alternative to hydrogen peroxide and sources thereof or in combination with hydrogen peroxide and sources thereof. Suitable classes include dialkylperoxides, diacylperoxides, preformed percarboxylic acids, organic and inorganic peroxides.

Typically, the compositions herein may comprise at least 0.01% by weight of the total composition of said peroxygen bleach or mixtures thereof, preferably from 0.1% to 15%, more preferably from 0.8% to 10% and most preferably 1% to 5%.

The compositions herein may further comprise a variety of other optional ingredients such builders, stabilisers, bleach activators, soil suspenders, dye transfer agents, brighteners, perfumes, anti dusting agents, enzymes, dispersant, dye transfer inhibitors, pigments, perfumes and dyes.

Packaging Form of the Disinfecting Compositions

The compositions herein may be packaged in a variety of suitable detergent packaging known to those skilled in the art.

In a preferred embodiment of the present invention, the liquid compositions herein are packaged in a plastic, preferably plastic, squeeze, container, preferably bottle.

Preferably, the disinfecting compositions herein in a liquid form may be packaged in manually operated spray dispensing containers. Accordingly, the present invention also encompasses liquid compositions of the invention packaged in a spray dispenser, preferably in a trigger spray dispenser or in a pump spray dispenser.

For example, said spray-type dispensers allow to uniformly apply to a relatively large area of a surface to be disinfected the liquid compositions suitable for use according to the present invention; thereby contributing to the disinfecting properties of said compositions. Such spray-type dispensers are particularly suitable to disinfect vertical surfaces.

Suitable spray-type dispensers to be used according to the present invention include manually operated foam trigger-type dispensers sold for example by Specialty Packaging Products, Inc. or Continental Sprayers, Inc. These types of dispensers are disclosed, for instance, in U.S. Pat. No. 4,701,311 to Dunnining et al. and U.S. Pat. No. 4,646,973 and U.S. Pat. No. 4,538,745 both to Facarracci. Particulaly preferred to be used herein are spray-type dispensers such as T 8500® or T8900® commercially available from Continental Sprayers International or T 8100® commercially available from Canyon, Northern Ireland. In such a dispenser the liquid composition is divided in fine liquid droplets resulting in a spray that is directed onto the surface to be treated. Indeed, in such a spray-type dispenser the composition contained in the body of said dispenser is directed through the spray-type dispenser head via energy communicated to a pumping mechanism by the user as said user activates said pumping mechanism. More particularly, in said spray-type dispenser head the composition is forced against an obstacle, e.g. a grid or a cone or the like, thereby providing shocks to help atomise the liquid composition, i.e. to help the formation of liquid droplets.

The compositions of the present invention may also be executed in the form of wipes. By "wipes", it is meant herein disposable towels incorporating a disinfecting composition according to the present invention. Preferably said wipes are packaged in a plastic box. Accordingly, the present invention also encompasses wipes, e.g., disposable towels, incorporating a composition as described herein before. Preferably said wipes are impregnated/wetted with a liquid disinfecting composition as described herein. The advantage of this execution is a faster usage of a disinfecting composition by the user, this even outside the house, i.e., there is no need for example to pour the liquid compositions according to the present invention on the surfaces to be disinfected and to dry it out with a cloth. In other words, wipes allow disinfecting of surfaces in one step.

EXPERIMENTAL DATA AND EXAMPLES

The following Examples are meant to exemplify compositions used in a process according to the present invention but are not necessarily used to limit or otherwise define the scope of the present invention.

Data on the Benefits Associated with the Compositions of the Present Invention

The following compositions were made by mixing the listed ingredients in the listed proportions (weight % unless otherwise specified). The compositions were then used in a process according to the present invention to disinfect a hard-surface.

| Ingredients | I (% w/w) | II (% w/w) | III (% w/w) | IV (% w/w) | V (% w/w) | VI (% w/w) |
|---|---|---|---|---|---|---|
| Water | to balance | to balance | to balance | to balance | to balance | to balance |
| Thymol | — | 0.01 | 0.01 | — | — | 0.01 |
| Geraniol | — | 0.09 | 0.29 | — | — | 0.09 |
| Cinnamon oil | — | — | — | — | 0.2 | 0.2 |
| Cinnamyl aldehyde | — | — | — | 0.2 | — | — |
| Perfume | 0.0375 | 0.1 | 0.1 | 0.1 | 0.1 | 0.15 |
| Ethanol | 9.4 | 9.4 | 5.0 | 9.4 | 8.0 | 8.0 |
| Silicone Dow AF | — | 0.003 | — | 0.003 | 0.003 | 0.003 |
| $C_{12-14}$ amine oxide | — | 0.2 | 0.2 | — | 0.1 | — |
| $C_{10}$ amine oxide | — | — | — | 0.2 | — | 0.02 |

-continued

| Ingredients | I (% w/w) | II (% w/w) | III (% w/w) | IV (% w/w) | V (% w/w) | VI (% w/w) |
|---|---|---|---|---|---|---|
| $C_{9-10}$ EO10 | 1.0 | 0.2 | — | 0.8 | 0.1 | — |
| $C_{9-11}$ EO5 | — | — | — | — | — | 0.1 |
| $C_{12-14}$ Betaine sodium salt | 0.25 | — | — | — | — | — |
| 2-Ethyl-Hexyl-Sulphate | 0.75 | 0.1 | 0.1 | 0.15 | 0.05 | 0.05 |
| Citric acid | 1.5 | 0.75 | 1.5 | 1.0 | — | — |
| Lactic acid | — | — | — | — | 0.44 | — |
| $Na_2CO_3$ | — | 0.1 | — | — | 0.06 | — |
| NaOH | up to pH 10.0 | up to pH 10.0 | up to pH 10.0 | up to pH 10.0 | up to pH 10.0 | up to pH 10.0 |
| Disinfection performance | Lg. Red | Lg. Red | Lg. Red | Lg. Red | Lg. Red | Lg. Red |
| Gram negative bacterial strain (*P. aeruginosa*) | 0.9 | 1.6 | 2.0 | 4.0 | 4.1 | 4.6 |
| Gram positive bacterial strain (*S. aureus*) | 1.5 | 1.7 | 3.7 | 4.5 | 4.5 | 4.8 |

The compositions I–VI described above were tested using test EN1276 as described in the section titled Disinfecting test method herein. Composition I–III are comparative examples. Compositions IV to VI are compositions according to the present invention.

The above results clearly show the disinfecting benefits both on gram negative and gram positive bacterial strains of a composition according to the present invention (compositions IV to VI), i.e., compositions comprising cinnamon oil or an active thereof, versus compositions comprising no essential oil or active thereof (composition I) or compositions comprising other essential oil or active thereof than cinnamon oil or an active thereof (composition II and III).

EXAMPLES

The following examples will further illustrate the present invention. The compositions are made by combining the listed ingredients in the listed proportions (weight % unless otherwise specified). Furthermore, the compositions I to L are comparative example compositions.

| Ingredients | A (% w/w) | B (% w/w) | C (% w/w) | D (% w/w) | E (% w/w) | F (% w/w) |
|---|---|---|---|---|---|---|
| Water | to balance | to balance | to balance | to balance | to balance | to balance |
| Thymol | 0.025 | — | — | — | 0.02 | — |
| Geraniol | 0.0375 | — | 0.3 | — | — | 0.1 |
| Cinnamic acid | — | 0.5 | — | — | — | — |
| Cinnamyl aldehyde | — | — | 0.3 | — | — | 0.2 |
| Vantocil IB ® | — | — | 0.3 | — | 0.1 | — |
| Chlrohexidine ® | — | — | — | 0.2 | 0.1 | — |
| Perfume | 0.0375 | 0.1 | 0.1 | 0.1 | 0.1 | 0.15 |
| Ethanol | 9.4 | 9.4 | 5.0 | 9.4 | 8.0 | 8.0 |
| Silicone Dow AF | — | 0.003 | — | 0.003 | 0.003 | 0.003 |
| $C_{12-14}$ amine oxide | — | 0.2 | 0.2 | — | 0.1 | — |
| $C_{10}$ amine oxide | — | — | — | 0.2 | — | 0.02 |
| $C_{9-10}$ EO10 | 1.0 | 0.2 | — | 0.8 | 0.1 | — |
| $C_{9-11}$ EO5 | — | — | — | — | — | 0.1 |
| $C_{12-14}$ Betaine sodium salt | 0.25 | — | — | — | — | — |
| 2-Ethyl-hexyl-Sulphate | 0.75 | 0.1 | 0.1 | 0.15 | 0.05 | 0.05 |
| Citric acid | 1.5 | 0.75 | 1.5 | 1.0 | — | — |
| Lactic acid | — | — | — | — | 0.44 | — |
| Na2CO3 | — | 0.1 | — | — | 0.06 | — |
| NaOH | — | 0.45 | — | — | 0.2 | — |
| pH | 2.4 | 9.5 | 2.8 | 2.8 | 9.5 | 7.1 |

-continued

| Ingredients | G (% w/w) | H (% w/w) | I (% w/w) | J (% w/w) | K (% w/w) | L (% w/w) |
|---|---|---|---|---|---|---|
| Water | to balance | to balance | to balance | to balance | to balance | to balance |
| Cinnamon oil | — | — | — | — | 0.2 | 0.1 |
| Cinnamic acid | 0.1 | — | 0.2 | — | — | — |
| Cinnamyl aldehyde | — | 0.1 | — | 0.3 | — | — |
| Thymol | 0.025 | — | — | — | — | — |
| Geraniol | 0.0375 | — | 0.3 | — | — | — |
| Vantocil IB ® | — | — | — | 0.3 | — | 0.2 |
| Chlrohexidine ® | — | — | — | — | 0.5 | — |
| Perfume | 0.0375 | 0.1 | 0.1 | 0.1 | 0.1 | 0.15 |
| Ethanol | 9.4 | 9.4 | 5.0 | 9.4 | 8.0 | 8.0 |
| Silicone Dow AF | — | 0.003 | — | 0.003 | 0.003 | 0.003 |
| $C_{12-14}$ amine oxide | — | 0.2 | 0.2 | — | 0.1 | — |
| $C_{10}$ amine oxide | — | — | — | 0.2 | — | 0.02 |
| $C_{9-10}$ EO10 | 1.0 | 0.2 | — | 0.8 | 0.1 | — |
| $C_{9-11}$ EO5 | — | — | — | — | — | 0.1 |
| $C_{12-14}$ Betaine sodium salt | 0.25 | — | — | — | — | — |
| 2-Ethyl-hexyl-Sulphate | 0.75 | 0.1 | 0.1 | 0.15 | 0.05 | 0.05 |
| Citric acid | 1.5 | 0.75 | 1.5 | 1.0 | — | — |
| Lactic acid | — | — | — | — | 0.44 | — |
| $Na_2CO_3$ | — | 0.1 | — | — | 0.06 | — |
| NaOH | — | 0.45 | — | — | 0.2 | — |
| pH | 2.4 | 9.5 | 2.8 | 2.8 | 9.5 | 7.1 |

Vantocil IB ® is poly (hexamethylene biguanide) hydrochloride commercially available from ICI.
Chlrohexidine ® is 1,1'-hexamethylene-bis-[5-(p-chlorphenyl)-biguanide] commercially available from Sigma.

What is claimed is:

1. A method of disinfecting a hard-surface comprising the step of:
   contacting said surface with a cleaning wipe impregnated with a composition comprising:
   (a) cinnamon oil and/or an active thereof wherein said cinnamon oil is selected from the group consisting of: cinnamic acid (C6H5CH=CHCOOH; 3-phenyl-2-propenoic acid); cinnamyl aldehyde (C6H5CH=CHCHO; 3-phenyl-2-propenal); cinnamyl alcohol (C6H5CH=CHCH2OH; 3-phenyl-2-propen-1-ol); dehydro-cinnamyl aldehyde; amyl cinnamyl aldehyde; hexyl cinnamyl aldehyde; hexyl cinnamyl aldehyde; a-n-butyl cinnamyl aldehyde and mixtures thereof; and
   (b) from 0.01% to 5.0% by weight of an organic acid or a salt thereof or a mixture thereof.

2. The method of claim 1, wherein said composition comprises up to 20% by weight of the total composition of cinnamon oil and/or an active thereof.

3. The method of claim 1, wherein said composition further comprises an essential oil or an active thereof or a mixture thereof in addition to said cinnamon oil or active thereof.

4. The method of claim 3, wherein said composition comprises up to 20% by weight of the total composition of said essential oil or an active thereof or a mixture thereof in addition to said cinnamon oil or active thereof.

5. The method of claim 3, wherein said essential oil is selected from the group consisting of oils obtained from thyme, lemongrass, citrus, lemons, oranges, anise, clove, aniseed, cinnamon, geranium, roses, mint, lavender, citronella, eucalyptus, peppermint, camphor, sandalwood, pine, vervain, rosmarin, fleagrass, ratanhiae, cedar and mixtures thereof; and wherein said or an active thereof is selected from the group consisting of actives of essential oils consisting of thymol, eugenol, menthol, geraniol, verbenone, eucalyptol, pinocarvone, cedrol, anethol, cinnamic acid, cinnamic aldehyde, carvacrol, hinokitiol, berberine, ferulic acid, methyl salicylic acid, methyl salicylate terpineol and mixtures thereof.

6. The method of claim 1, wherein said composition comprises a binary essential oil comprising cinnamon oil and a first additional essential oil, said first additional essential oil being selected from the group consisting of thymol, geraniol, eugenol and mixtures thereof.

7. The method of claim 1, wherein said composition comprises a ternary essential oil system comprising cinnamon oil, a first additional essential oil and a second additional essential oil.

8. The method of claim 1, wherein said composition further comprises a disinfecting material.

9. The method of claim 8, wherein said composition comprises from about 0.001% to about 40% by weight of the total composition of said disinfecting material.

10. The method of claim 1, wherein said composition further comprises an additional ingredient selected from the group consisting of solvents, surfactants, peroxygen bleaches, radical scavengers, chelating agents and mixtures thereof.

* * * * *